US012631633B2

(12) United States Patent (10) Patent No.: US 12,631,633 B2
Sivertsen (45) Date of Patent: May 19, 2026

(54) STANDARDIZED ASSAY TUBE AND REAGENT CAP

(71) Applicant: Assaya LLC, Roswell, GA (US)

(72) Inventor: Clas Sivertsen, Lilburn, GA (US)

(73) Assignee: ASSAYA LLC, Lakeside, MT (US)

( * ) Notice: Subject to any disclaimer, the term of this patent is extended or adjusted under 35 U.S.C. 154(b) by 870 days.

(21) Appl. No.: 17/536,038

(22) Filed: Nov. 28, 2021

(65) Prior Publication Data

US 2023/0168246 A1 Jun. 1, 2023

(51) Int. Cl.
G01N 33/543 (2006.01)
B01L 3/00 (2006.01)
G01N 33/569 (2006.01)

(52) U.S. Cl.
CPC ........ G01N 33/54389 (2021.08); B01L 3/523 (2013.01); G01N 33/56983 (2013.01); *B01L 2200/16* (2013.01); *B01L 2300/042* (2013.01); *B01L 2300/069* (2013.01); *B01L 2300/0825* (2013.01); *B01L 2300/0832* (2013.01); *G01N 2800/26* (2013.01)

(58) Field of Classification Search
None
See application file for complete search history.

(56) References Cited

U.S. PATENT DOCUMENTS

| | | | |
|---|---|---|---|
| 5,075,078 A | 12/1991 | Osikowicz et al. | |
| 5,308,775 A | 5/1994 | Donovan et al. | |
| 5,717,778 A | 2/1998 | Chu et al. | |
| 5,875,258 A | 2/1999 | Ortyn et al. | |
| 5,968,839 A | 10/1999 | Blatt et al. | |
| 6,061,128 A | 5/2000 | Zweig et al. | |
| 6,267,722 B1 | 7/2001 | Anderson et al. | |
| 6,394,952 B1 | 5/2002 | Anderson et al. | |
| 6,664,071 B1 | 12/2003 | Windhab et al. | |
| 7,177,235 B2 | 2/2007 | Rund | |
| 7,236,428 B1 | 6/2007 | Morse | |
| 7,267,799 B1 | 9/2007 | Borich et al. | |
| 9,702,872 B1 | 7/2017 | Wang et al. | |
| 9,857,372 B1 | 1/2018 | Pulitzer et al. | |
| 9,857,373 B1 | 1/2018 | Pulitzer et al. | |
| 10,197,558 B1 | 2/2019 | Saaski et al. | |
| 10,823,746 B1 | 11/2020 | Busa et al. | |
| 11,740,203 B2 | 8/2023 | Galen et al. | |
| 11,802,868 B2 | 10/2023 | Pulitzer et al. | |
| 12,094,603 B2 * | 9/2024 | Sivertsen | G16H 40/63 |
| 12,311,065 B1 | 5/2025 | Miller | |
| 2001/0053336 A1 | 12/2001 | Hammer et al. | |
| 2003/0021726 A1 | 1/2003 | Wu et al. | |
| 2003/0040128 A1 | 2/2003 | Meador et al. | |
| 2003/0120633 A1 | 6/2003 | Torre-Bueno | |
| 2003/0139903 A1 | 7/2003 | Zweig et al. | |
| 2003/0143530 A1 | 7/2003 | Klepp et al. | |
| 2004/0122790 A1 | 6/2004 | Walker et al. | |
| 2005/0008538 A1 | 1/2005 | Anderson et al. | |

| | | | |
|---|---|---|---|
| 2005/0203353 A1 | 9/2005 | Ma et al. | |
| 2005/0255001 A1 | 11/2005 | Padmanabhan et al. | |
| 2005/0255600 A1 | 11/2005 | Padmanabhan et al. | |
| 2006/0216832 A1 | 9/2006 | Nishikawa et al. | |
| 2006/0223192 A1 | 10/2006 | Smith et al. | |
| 2006/0246599 A1 | 11/2006 | Rosenstein et al. | |
| 2006/0274145 A1 | 12/2006 | Reiner | |
| 2006/0292040 A1 | 12/2006 | Wickstead et al. | |
| 2007/0122914 A1 | 5/2007 | Curry | |
| 2007/0143035 A1 | 6/2007 | Petruno | |
| 2008/0138842 A1 | 6/2008 | Boehringer et al. | |
| 2008/0186499 A1 | 8/2008 | Krauth | |
| 2009/0061450 A1 | 3/2009 | Hunter | |
| 2009/0074282 A1 | 3/2009 | Pinard et al. | |
| 2009/0087926 A1 | 4/2009 | Hasegawa et al. | |
| 2009/0155811 A1 | 6/2009 | Natan et al. | |
| 2009/0312663 A1 | 12/2009 | John et al. | |
| 2010/0045789 A1 | 2/2010 | Fleming et al. | |
| 2010/0099115 A1 * | 4/2010 | Mach | G01N 1/38 435/7.1 |
| 2010/0105024 A1 | 4/2010 | Xu et al. | |
| 2010/0135857 A1 | 6/2010 | Hunter et al. | |
| 2010/0267049 A1 | 10/2010 | Rutter et al. | |
| 2010/0331651 A1 | 12/2010 | Groll | |
| 2011/0213564 A1 | 9/2011 | Henke | |

(Continued)

FOREIGN PATENT DOCUMENTS

| | | |
|---|---|---|
| CN | 102482702 A | 5/2012 |
| CN | 102539735 A | 7/2012 |

(Continued)

OTHER PUBLICATIONS

Thao et al. (American Clinical Society, 2017, p. 6781-6786).*
Grant et al. (May 7, 2020, Intellectual Ventures Lab, p. 1-11).*
Anfossi et al., Multiplex Lateral Flow Immunoassay: An Overview of Strategies towards High-throughput Point-of-Need Testing, Biosensors (Basel). Mar. 2019; 9(1): 2. (Year: 2018).
Assaygenie, Rapid covid19 antibody detection test principles and methods, published: 2020, https://www.assaygenie.com/rapid-covid 19-antibody-detection-tests-principles-and-methods (Year: 2020).

(Continued)

*Primary Examiner* — Agnieszka Boesen

(74) *Attorney, Agent, or Firm* — Nicholson De Vos Webster & Elliott LLP; Judith Szepesi

(57) ABSTRACT

Embodiments of the present invention are directed to a test kit. The test kit includes an assay tube and a reagent cap. The assay tube includes a sample opening in the assay tube for receiving a sample and a lateral flow assay ("LFA") test strip in the assay tube in communication with a sample opening. The reagent cap is designed to be placed over the assay tube and includes a buffer. When the reagent cap is placed over the sample opening of the assay tube the buffer is released over the sample to carry an analyte over the LFA test strip.

20 Claims, 10 Drawing Sheets

(56) References Cited

U.S. PATENT DOCUMENTS

| | | |
|---|---|---|
| 2011/0213579 A1 | 9/2011 | Henke |
| 2012/0071342 A1 | 3/2012 | Lochhead et al. |
| 2012/0115214 A1 | 5/2012 | Battrell et al. |
| 2012/0122236 A1 | 5/2012 | Tarpey |
| 2012/0123686 A1 | 5/2012 | Xiang et al. |
| 2012/0281970 A1 | 11/2012 | Garibaldi et al. |
| 2012/0282154 A1 | 11/2012 | Slowey et al. |
| 2013/0203043 A1 | 8/2013 | Ozcan et al. |
| 2013/0273645 A1 | 10/2013 | Waga |
| 2013/0288254 A1 | 10/2013 | Pollack et al. |
| 2013/0338243 A1 | 12/2013 | Kentsis et al. |
| 2014/0014720 A1 | 1/2014 | Sarkis, Jr. et al. |
| 2014/0017812 A1 | 1/2014 | Smith et al. |
| 2014/0018779 A1 | 1/2014 | Worrell et al. |
| 2014/0154792 A1 | 6/2014 | Moynihan et al. |
| 2014/0227681 A1 | 8/2014 | Fleming et al. |
| 2014/0278832 A1 | 9/2014 | Glavina et al. |
| 2014/0324373 A1 | 10/2014 | Xiang et al. |
| 2014/0339100 A1 | 11/2014 | Malecha |
| 2015/0010992 A1 | 1/2015 | Fleming et al. |
| 2015/0099306 A1 | 4/2015 | Ku |
| 2015/0244852 A1 | 8/2015 | Erickson et al. |
| 2015/0310182 A1 | 10/2015 | Henze et al. |
| 2015/0338387 A1 | 11/2015 | Ehrenkranz |
| 2015/0350605 A1 | 12/2015 | Price et al. |
| 2016/0030613 A1 | 2/2016 | Paul et al. |
| 2016/0085913 A1 | 3/2016 | Evans et al. |
| 2016/0131645 A1* | 5/2016 | Wang .................... B01L 3/5023 |
| | | 435/287.7 |
| 2016/0157598 A1 | 6/2016 | Anelevitz |
| 2016/0178607 A1 | 6/2016 | Husheer et al. |
| 2016/0188937 A1 | 6/2016 | Tyrrell et al. |
| 2016/0265032 A1 | 9/2016 | Sethi et al. |
| 2016/0356800 A1 | 12/2016 | Glavina et al. |
| 2016/0356801 A1 | 12/2016 | Glavina et al. |
| 2016/0370366 A1 | 12/2016 | Fleming et al. |
| 2017/0049915 A1 | 2/2017 | Brais et al. |
| 2017/0160258 A1 | 6/2017 | Hengstler et al. |
| 2017/0184586 A1 | 6/2017 | Hopper |
| 2018/0031551 A1 | 2/2018 | Karlovac et al. |
| 2018/0052916 A1 | 2/2018 | Abebe et al. |
| 2018/0071741 A1 | 3/2018 | Kelly et al. |
| 2018/0106789 A1 | 4/2018 | Pulitzer et al. |
| 2018/0107790 A1 | 4/2018 | Pulitzer et al. |
| 2018/0149600 A1 | 5/2018 | Farrell |
| 2018/0164222 A1 | 6/2018 | Pulitzer et al. |
| 2018/0246038 A1 | 8/2018 | Hunter |
| 2018/0259449 A1 | 9/2018 | Poulsen et al. |
| 2018/0293350 A1 | 10/2018 | Dimov et al. |
| 2018/0348198 A1 | 12/2018 | Broadwell |
| 2018/0372734 A1 | 12/2018 | Pfenninger et al. |
| 2019/0070324 A1 | 3/2019 | Hardin et al. |
| 2019/0096516 A1 | 3/2019 | Pulitzer et al. |
| 2019/0122768 A1 | 4/2019 | Pulitzer et al. |
| 2019/0224685 A1 | 7/2019 | Benenati |
| 2019/0229907 A1 | 7/2019 | Nicolson et al. |
| 2019/0267822 A1 | 8/2019 | Voit et al. |
| 2019/0317115 A1 | 10/2019 | Maclean et al. |
| 2019/0339264 A1 | 11/2019 | Gary et al. |
| 2019/0369094 A1 | 12/2019 | Ishikawa et al. |
| 2020/0217835 A1 | 7/2020 | Darmstadt et al. |
| 2020/0330979 A1 | 10/2020 | Cyr et al. |
| 2020/0386753 A1 | 12/2020 | Somes et al. |
| 2020/0408715 A1 | 12/2020 | Galen et al. |
| 2021/0086177 A1 | 3/2021 | Lin |
| 2021/0132035 A1 | 5/2021 | Adelman |
| 2021/0172945 A1 | 6/2021 | Armbruster et al. |
| 2021/0263018 A1 | 8/2021 | Taran |
| 2021/0293688 A1 | 9/2021 | Chang et al. |
| 2021/0319911 A1 | 10/2021 | Hall et al. |
| 2021/0327056 A1 | 10/2021 | Needham et al. |
| 2021/0389233 A1 | 12/2021 | Hatamian |
| 2022/0055036 A1 | 2/2022 | Tycon |
| 2022/0091114 A1 | 3/2022 | Levin et al. |
| 2022/0146508 A1 | 5/2022 | Roswech et al. |
| 2022/0178920 A1 | 6/2022 | Howard |
| 2022/0254027 A1 | 8/2022 | Lin et al. |
| 2022/0254133 A1 | 8/2022 | Adsul et al. |
| 2022/0258155 A1 | 8/2022 | Ren et al. |
| 2022/0296755 A1 | 9/2022 | Wurmfeld et al. |
| 2022/0304560 A1 | 9/2022 | Jackson et al. |
| 2022/0399109 A1 | 12/2022 | Sivertsen |
| 2022/0404354 A1 | 12/2022 | Robinson et al. |
| 2022/0405551 A1 | 12/2022 | Jain et al. |
| 2022/0412961 A1 | 12/2022 | Jolly et al. |
| 2023/0213452 A1 | 7/2023 | Minobe et al. |
| 2023/0274538 A1 | 8/2023 | Sia et al. |
| 2023/0351754 A1 | 11/2023 | Satish et al. |
| 2024/0363206 A1 | 10/2024 | Mayer |
| 2024/0387010 A1 | 11/2024 | Sivertsen et al. |
| 2024/0402198 A1 | 12/2024 | Sivertsen |
| 2024/0404658 A1 | 12/2024 | Sivertsen et al. |
| 2024/0412829 A1 | 12/2024 | Sivertsen et al. |
| 2024/0424160 A1 | 12/2024 | Sivertsen et al. |
| 2024/0428905 A1 | 12/2024 | Sivertsen |

FOREIGN PATENT DOCUMENTS

| | | | |
|---|---|---|---|
| CN | 104838383 A | 8/2015 |
| CN | 105022911 A | 11/2015 |
| CN | 106680496 A | 5/2017 |
| CN | 110312935 A | 10/2019 |
| CN | 211086092 U | 7/2020 |
| EP | 0480208 A2 | 4/1992 |
| EP | 2839264 A1 | 2/2015 |
| TW | 201833554 A | 9/2018 |
| TW | M588797 U | 1/2020 |
| WO | 2013/119266 A1 | 8/2013 |
| WO | 2013/158504 A1 | 10/2013 |
| WO | 2020/174895 A1 | 9/2020 |
| WO | 2020/251460 A1 | 12/2020 |

OTHER PUBLICATIONS

Azzi et al., Rapid Salivary Test suitable for a mass screening program to detect SARS-COV-2: A diagnostic accuracy study, Journal of Infection, vol. 81, Issue 3, Sep. 2020, Pages e75-e78 (Year: 2020).

Badi et al., The Effect of Gold Salt Concentration in the Production of Gold Nanospheres, Jan. 2020, Journal of Applied Mathematics and Physics (Year: 2020).

Baker et al., The SARS-COV-2 Spike Protein Binds Sialic Acids and Enables Rapid Detection in a Lateral Flow Point of Care Diagnostic Device, 2020, vol. 6, 2046-2052 (Year: 2020).

Contreras-Aguilar, Changes in Saliva Analytes in Dairy Cows during Peripartum: A Pilot Study, Mar. 9, 2021, Animals, vol. 11, issues 3 (Year: 2021).

Correa, M. E. et al., Pregnancy Hypertension: An International Journal of Women's Cardiovascular Health 2017, 750-53. (Year: 2017).

De Silva, D. A. et al., Journal of Obstetrics and Gynaecology Canada 2014, 36, 605-612. (Year: 2014).

Filippini, D. et al., Analyst 2006, 131, 111-117. (Year: 2006).

Hou, Y. et al., Nanoscale Research Letters 2017, 12, paper 291, 13 pages. (Year: 2017).

Independent Forensics, Developmental Validation of RSID-Urine, Mar. 2021, Independent Forensics, https://www.ifi-test.com/rsid-urine/ (Year: 2021).

Larsen et al., Fluorometric determination of uric acid in bovine milk, 2010, Journal of Dairy Research, vol. 77, 438-444 (Year: 2010).

Lin, C.-S. et al., Optik 2004, 115, 363-369. (Year: 2004).

Magiati, M et al., Microchimica Acta 2018, 185, paper 314, 9 pages. (Year: 2018).

O'Farrell, B., in Lateral Flow Immunoassay 2009, Wong, R. C et al. (eds.), Humana Press, New York, 1-33. (Year: 2009).

Old et al., Developmental Validation of RSIDTM-Saliva: A Lateral Flow Immunochromatographic Strip Test for the Forensic Detection of Saliva, J Forensic Sci, Jul. 2009, vol. 54, No. 4 (Year: 2009).

(56) References Cited

OTHER PUBLICATIONS

Panic, G. et al., Parasites & Vectors 2019, 12, paper 298, 7 pages. (Year: 2019).

Richardson et al., Amylase in Cow's Milk, 1936, Journal of Dairy Science, vol. 19, Issue 12, 761-772 (Year: 1936).

StatTechnologies, Adulteration Test Strips, 2017, StatTechnologies, https://stat-technologies.com/product/adulteration-test-strips/ (Year: 2017).

Stuart Patton, Some Practical Implications of the Milk Mucins, 1999, Journal of Dairy Science, vol. 82, Issue 6, 1115-1117 (Year:1999).

Tucker, K. et al., Pregnancy Hypertension 2018, 12, 161-168. (Year: 2018).

Urusov AE et al. (2019) Towards Lateral Flow Quantitative Assays: Detection Approaches. Biosensors, 9(3), 16 pgs; https://doi.org/10.3390/bios9030089 (Year: 2019).

Waters, L. C. et al., Journal of Hazardous Materials 1995, 43, 1-12. (Year: 1995).

Waugh, J. J. S. et al., BJOG: an International Journal of Obstetrics and Gynaecology 2005, 112, 412-417. (Year: 2005).

Xu, Y. et al., Analytical Chemistry 2018, 90, 708-715 with 13 pages of supporting information. (Year: 2018).

Zhou et al. Paper electrode integrated lateral flow immunosensor for quantitative analysis of oxidative stress induced DNA damage, 2014, Analyst, 139(11), 2850-2857 (Year: 2014).

* cited by examiner

310

320

410

420

145

150

STANDARDIZED ASSAY TUBE AND REAGENT CAP

BACKGROUND

The present invention generally relates to diagnostic testing and more specifically, to a standardized assay tube and reagent cap.

Coronavirus Disease 2019 ("COVID-19") is spreading throughout the world caused by the spread of a novel coronavirus called SARS-CoV-2. With the rapid spread of the disease, testing quickly, accurately, and efficiently is becoming more important. Testing is often performed by collecting a sample via swabbing the back of the nasal cavity with a nasopharyngeal swab or swabbing the throat of a patient and performing an analysis of the collected sample. A wide range of test kits are currently on the market each with varying size and each requiring a host of accoutrements in order to conduct a test. For example, a COVID-19 test kit may contain a test cassette, a nasopharyngeal swab, a reagent tube, a pipette, and a desiccant for each test kit.

SUMMARY

Embodiments of the present invention are directed to a test kit. The test kit includes an assay tube and a reagent cap. The assay tube includes a sample opening in the assay tube for receiving a sample and a lateral flow assay ("LFA") test strip in the assay tube in communication with a sample opening. The reagent cap is designed to be placed over the assay tube and includes a buffer. When the reagent cap is placed over the sample opening of the assay tube the buffer is released over the sample to carry an analyte over the LFA test strip.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

Figure 1:
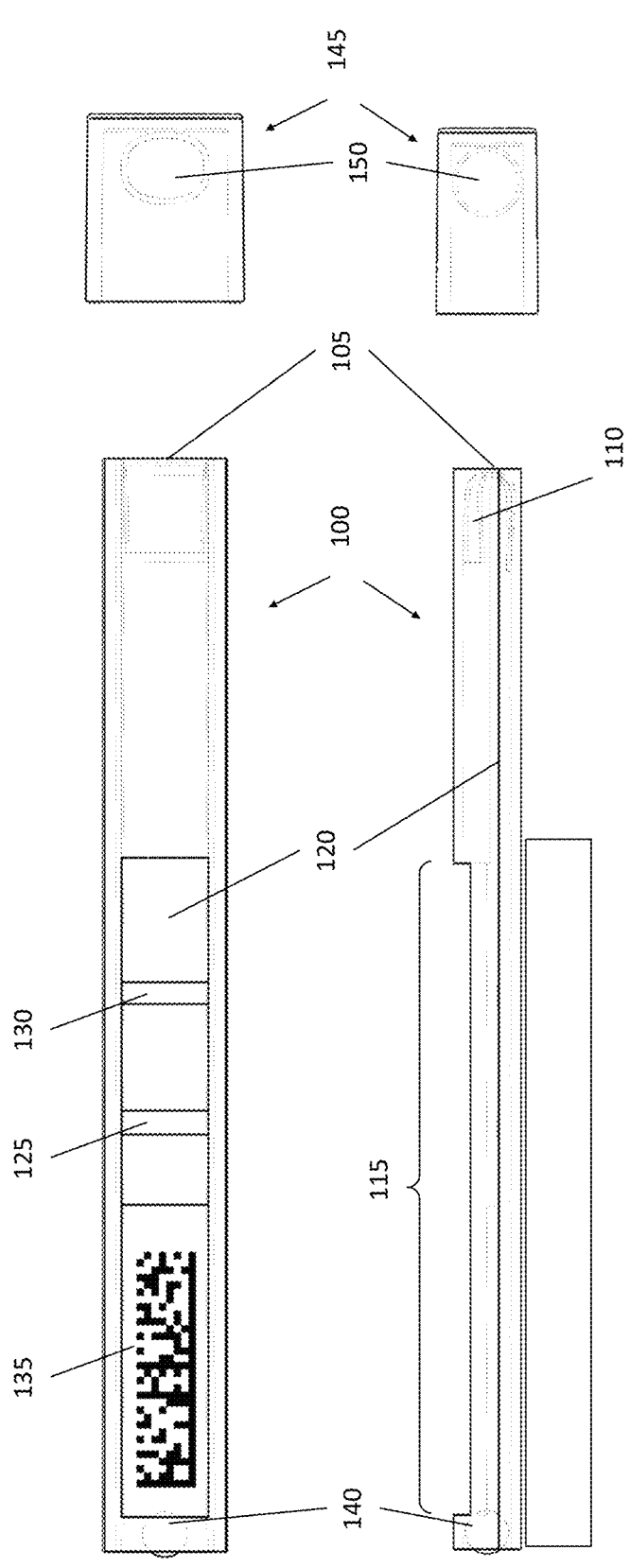
FIG. 1 depicts a top-down view and a side view of an assay tube and a reagent cap according to an embodiment of the present invention.

The diagrams depicted herein are illustrative. There can be many variations to the diagrams or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the disclosed embodiments, the various elements illustrated in the figures are provided with two- or three-digit reference numbers. With minor exceptions, the leftmost digit(s) of each reference number corresponds to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" may be understood to include any integer number greater than or equal to one, i.e. one, two, three, four, etc. The terms "a plurality" may be understood to include any integer number greater than or equal to two, i.e.

two, three, four, five, etc. The term "connection" may include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

Turning now to an overview of technologies that are more specifically relevant to aspects of the invention, as previously stated, SARS-CoV-2 is spreading rapidly around the country and around the world resulting in a large portion of the population being at risk of developing COVID-19. It is imperative to test, often repeatedly, the population for SARS-CoV-2, and present test kits are inefficient, wasteful, and costly.

Antigen testing is used to test for SARS-CoV-2. Typically, A nasopharyngeal or nasal swab is inserted into the nose of a patient and samples of the patient's epithelial cells are collected on the swab as it is removed from the patient's nose. The swab is then placed into a tube having a buffer. The buffer contains detergent, a lysing component to open the sample cells to get cytoplasm out of the cells, and a buffer agent. A pipette is then used to draw an analyte from the tube and place a few drops of analyte onto the analyte pad of an LFA strip in a test cassette. An antibody bound with a color particle on a test line of the LFA strip will combine with any antigen present in the analyte, releasing the color particle to color the test strip to indicate the presence of the antigen, i.e. a positive test result. This process and these components generate a lot of medical and plastic waste. It is also costly to package each of these components together into each test kit, which also increases weight thus transportation costs.

Antibody testing is performed in a similar fashion, but with an antigen or receptor protein bound to a color particle used as the marker. Antibody testing is traditionally done using centrifuged venous blood (serum), although some newer types of tests can use blood from a finger prick as described below. Whether antibody or antigen, both are chemical markers—a piece of chemistry that is being looked for. Biological markers such as proteins may also be looked for, such as in pregnancy tests. Also, non-organic chemical markers may be looked for such as arsenic or chlorine in pools, for example. All are chemical markers.

Finger pricks may also be used for antibody and antigen testing. A lancet is used to draw the blood from the finger to produce blood. A capillary straw having a ten microliter mark draws blood which is then expelled by the straw onto an LFA strip. The buffer used when testing venous blood contains an anticoagulating agent and an anti red blood cell filtration component, so that mostly only serum makes its way up the LFA strip to the testing site on the LFA strip. Again, this system also has additional medical waste in the form of the lancet for pricking the finger and the capillary straw and their associated packaging.

Turning now to an overview of the aspects of the invention, one or more embodiments of the invention address the above-described shortcomings of the prior art by providing a uniquely coded testing assay tube containing a lateral flow assay ("LFA") test strip and a desiccant. The assay tube receives a sample directly from a patient at an opening of the tube and a reagent cap containing a buffer is placed over the opening causing the buffer to wash over the sample carrying an analyte onto and over the LFA test strip. By using the combination assay tube and reagent cap, medical and plastic waste is significantly reduced. The need for a nasopharyngeal swab or other swab for a mouth, a tube to hold a buffer solution in which the swab is inserted, and a pipette to draw analyte out of the tube is eliminated. Also, as a small desiccant is located inside the assay tube, the need for large packets of external desiccant beds or strips is also eliminated, thus further reducing waste and costs.

In contrast to prior testing methodologies, the assay tube described herein can also be used for testing for mucosal antibodies, such as Immunoglobulin A, by scraping a subject's gingiva.

Furthermore, by standardizing a size of the assay tube and reagent cap dispensing of packages of test kits is improved because the helter skelter sizing of test kits is done away with. Additionally, as the size of the assay tube and reagent cap are quite small when compared with prior art test kits, plastic and medical waste is even further reduced.

While the discussion in this description uses testing for SARS-CoV-2 to discuss embodiments of the invention, those skilled in the art after reading this specification will appreciate that similar techniques can be used for testing for a variety of markers, both chemical, biological, and non-organic.

Figure 3:
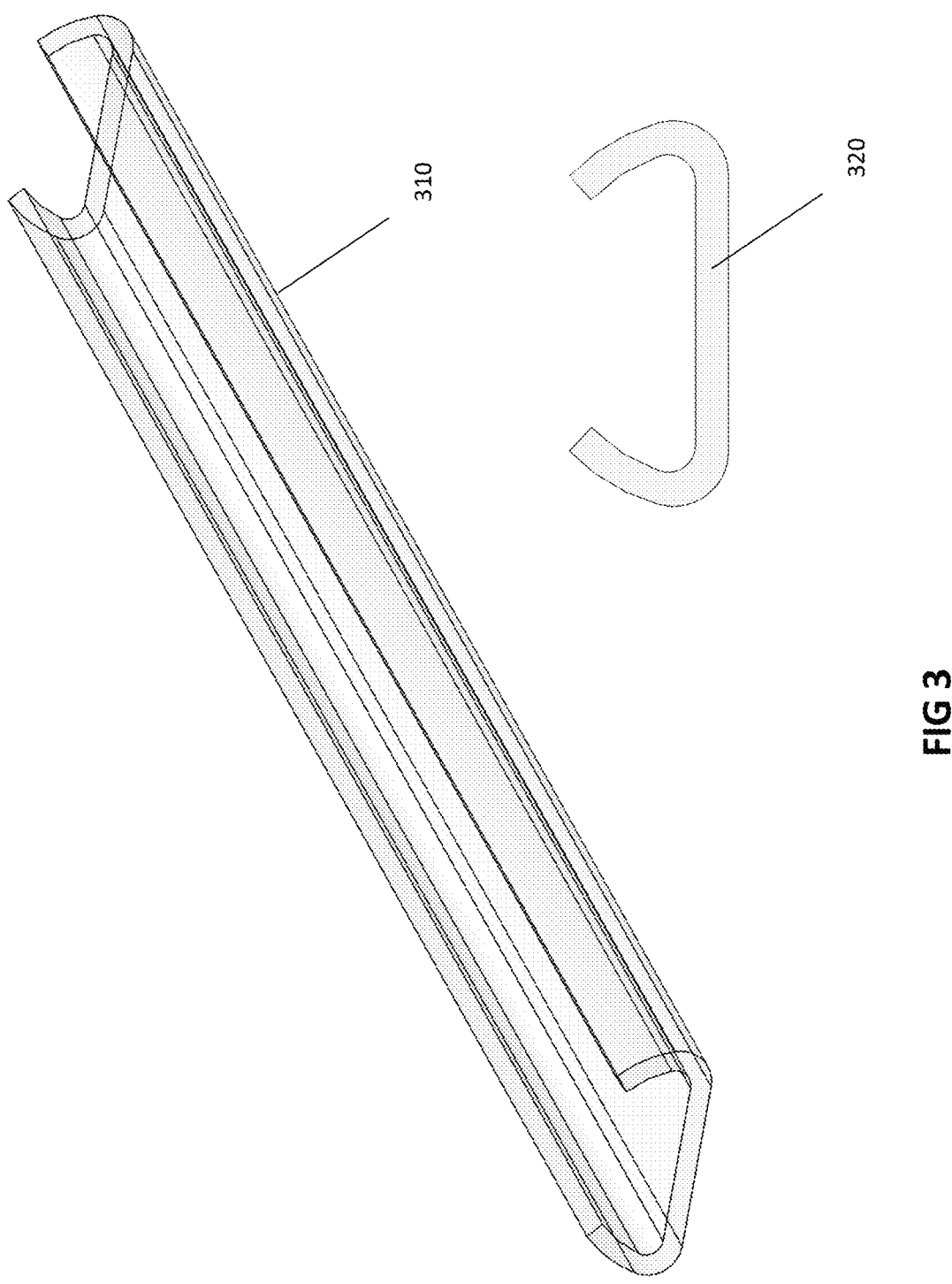
FIG. 3 depicts an orthogonal view of an external portion of a curved assay tube according to embodiments of the present invention.
Figure 4:
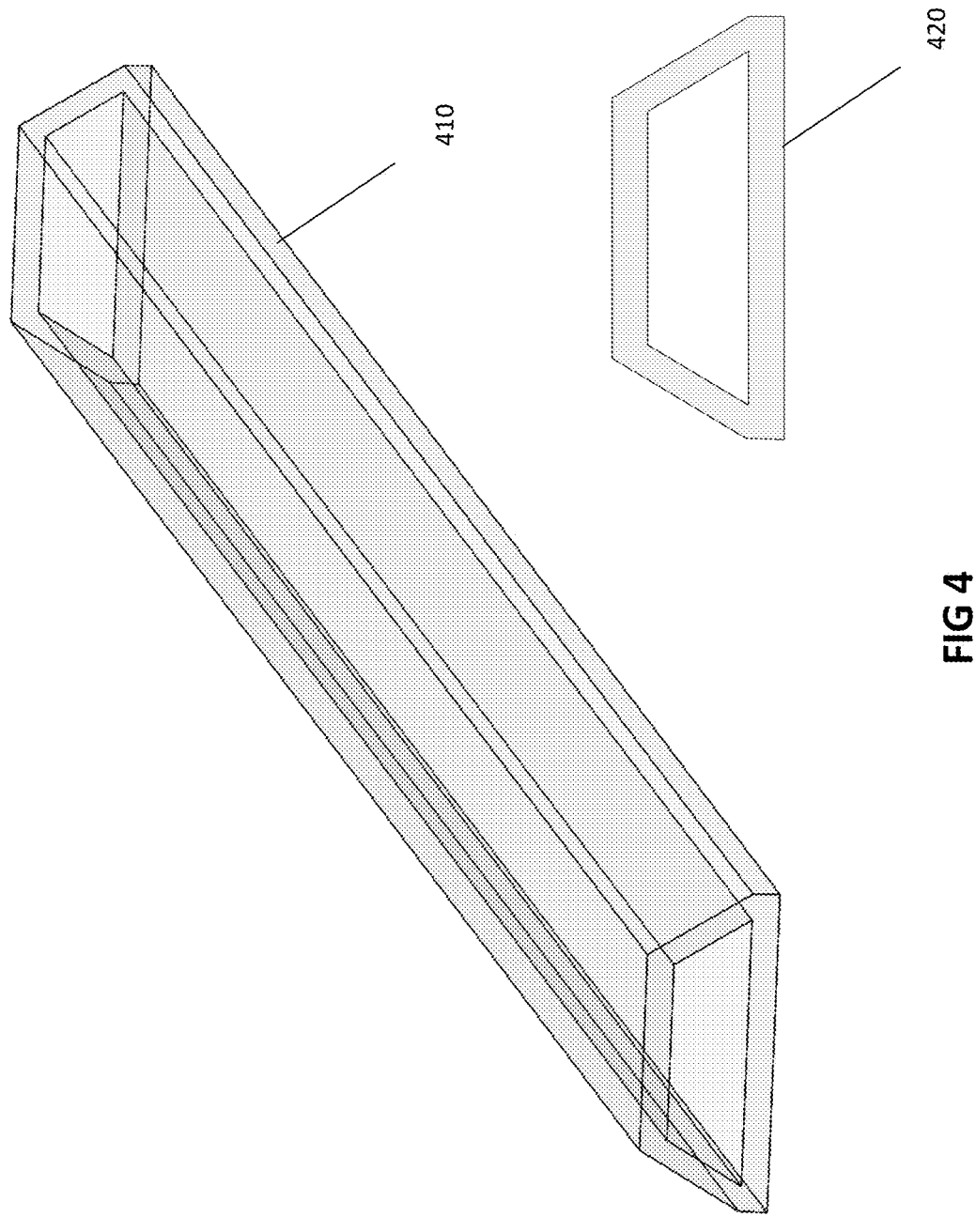
FIG. 4 depicts an orthogonal view of an external portion of a trapezoidal assay tube according to embodiments of the present invention.

FIG. 1 depicts a top-down view and a side view of an assay tube 100 and a reagent cap 145 according to an embodiment of the present invention. The assay tube 100 includes a polyethylene ("PE"), polypropylene ("PP"), or polymethyl methacrylate ("PMMA") tube (typically made by extrusion) 105 that is elongated and has a semicircular cross-section. Materials other than PE, PP, and PMMA can be used, and those skilled in the art after reading this disclosure will appreciate that a wide range of other materials can be used in place of PE, PP, or PMMA for the tube. The assay tube 100 has a sample opening 105 for receiving a combination of a sample and, later when the reagent cap 145 is placed over the assay tube 100, a buffer. Other embodiments could have a rectangular, trapezoidal, or square cross-section, for example, and those skilled in the art will appreciate after reading this disclosure that any cross-sectional shape can be used. FIGS. 3 and 4 illustrate exemplary additional cross-sectional shapes. However, it proves advantageous to have at least a portion of the cross-sectional shape be flattened, so that the assay tube 100 may be placed on a surface without rolling. It is contemplated that round, or non-flattened, assay tubes 100 may be used in conjunction with surfaces shaped to receive non-flattened assay tubes 100. Thus, "assay tube" has a broader meaning than the conventional meaning of a tube, as an "assay tube" includes tubes having cross-sections that are not continuous or fully enclosed. For example, the open design shown in FIG. 3 is still an "assay tube."

Where the assay tube 100 is made from a material that is opaque, a viewing opening 115 is created, typically by cutting, into the assay tube 100 during manufacture. The opening allows for clear viewing of an LFA test strip 120 that is located within the assay tube 100. The LFA test strip 120 may include a unique identifier 135 that uniquely identifies the assay tube 100, such as a data matrix, and one or more control lines 125 and test lines 130. An absorbent material 110 such as dental cotton may be placed in the bottom of the assay tube 100. The absorbent material 100 may be useful in a number of use cases, including when sample is collected by the assay tube 100 through a patient blowing into the sample opening 105. In that case, the absorbent material 110 will collect patient sample cells which will later be washed over the LFA test strip 120 as an analyte when buffer is placed into the assay tube 100.

When the assay tube 100 is made from a clear material, no viewing opening 115 is required, and the assay tube 100 may lack viewing opening 115. A desiccant 140, such as a desiccant gel, is placed in the assay tube 100 to absorb moisture that might spoil the LFA test strip 120 prior to use. The desiccant 140 may comprise a desiccant material that changes color in the presence of moisture, so that a technician or patient can see that the LFA test strip 120 is spoiled or been previously used, e.g., having been blown into, and should not be used for a new test. In addition, the color-changing desiccant can be used for fraud or mistake purposes to indicate that a patient has actually blown into a tube with sufficient air volume. For example, it may turn blue in the presence of moisture.

Returning to the sample opening 105, a portion of the sample opening 105 may be roughened to, for example, draw saliva or mucus from the patient's tongue or oral mucosa. The purpose of the roughened surface is to collect epithelial cells from the tongue surface by scraping the clear assay across the dorsal, lateral, or ventral surfaces of the tongue or gingiva. The degree of roughness will vary depending on what part of a patient is being tested. For example, when testing nasal passages the degree of roughness may be less than when testing the oral cavity.

The sample taken into the sample opening may be any type of sample containing chemical markers. For example, biological markers taken from a patient's nose, mouth, skin, vagina, anus, stool, urine, or venous blood (stool and urine collectively referred to as "excreta") may be received. As another example, water samples may be taken from a pool to check for chlorine or from a stream to check for toxins such as arsenic. There are no limits on the types of samples taken.

The reagent cap 145 contains a buffer, typically placed in a capsule 150 located within the reagent cap 145. After a sample is collected in the sample opening 105 of the assay tube 100, the reagent cap 145 is placed over the sample opening 105 of the assay tube 100 which causes the capsule 150 to burst, releasing the buffer to wash over the sample carrying analyte onto the LFA test strip 120.

In an alternative embodiment shown and described later, in place of a capsule 150 the buffer is placed directly into the reagent cap which is then sealed with a film cover to maintain the buffer in the reagent cap 145. The film cover is broken when the reagent cap 145 is placed over the assay tube 100 causing the buffer to be released and perform its washing and other actions.

A previously described the assay tube 100 and reagent cap 145 is substantially less polluting than prior art kits, and produces much less plastic and biologically hazardous waste compared to cassettes containing LFA strips. Because this solution eliminates the need for intermediary collection devices, the amount of waste generated is substantially less.

Returning to the printed symbology 135, the unique identifier 135 uniquely identifies the assay tube 100 and the sample, connecting it to the patient. The unique identifier may be a serialized, for example, identifier. In an exemplary embodiment of the invention, the barcode is a data matrix format based on ISO/IEC 16022:2006(E). A manufacturer code, supplier code, profile code (denoting disease being tested for), year code, day code, and serial number may be encoded in the symbology 135. When a patient is provided with the assay tube 100, her information may be entered into a central database along with a scan of the barcode, thus linking them together. In alternative embodiment of the invention, the unique identifier 135 is placed on the outside of the assay tube 100 instead of on the LFA test strip 120. In another alternative embodiment of the invention, the unique identifier 135 is within the assay tube 100, but not mounted directly on the LFA test strip 120.

Figure 2:
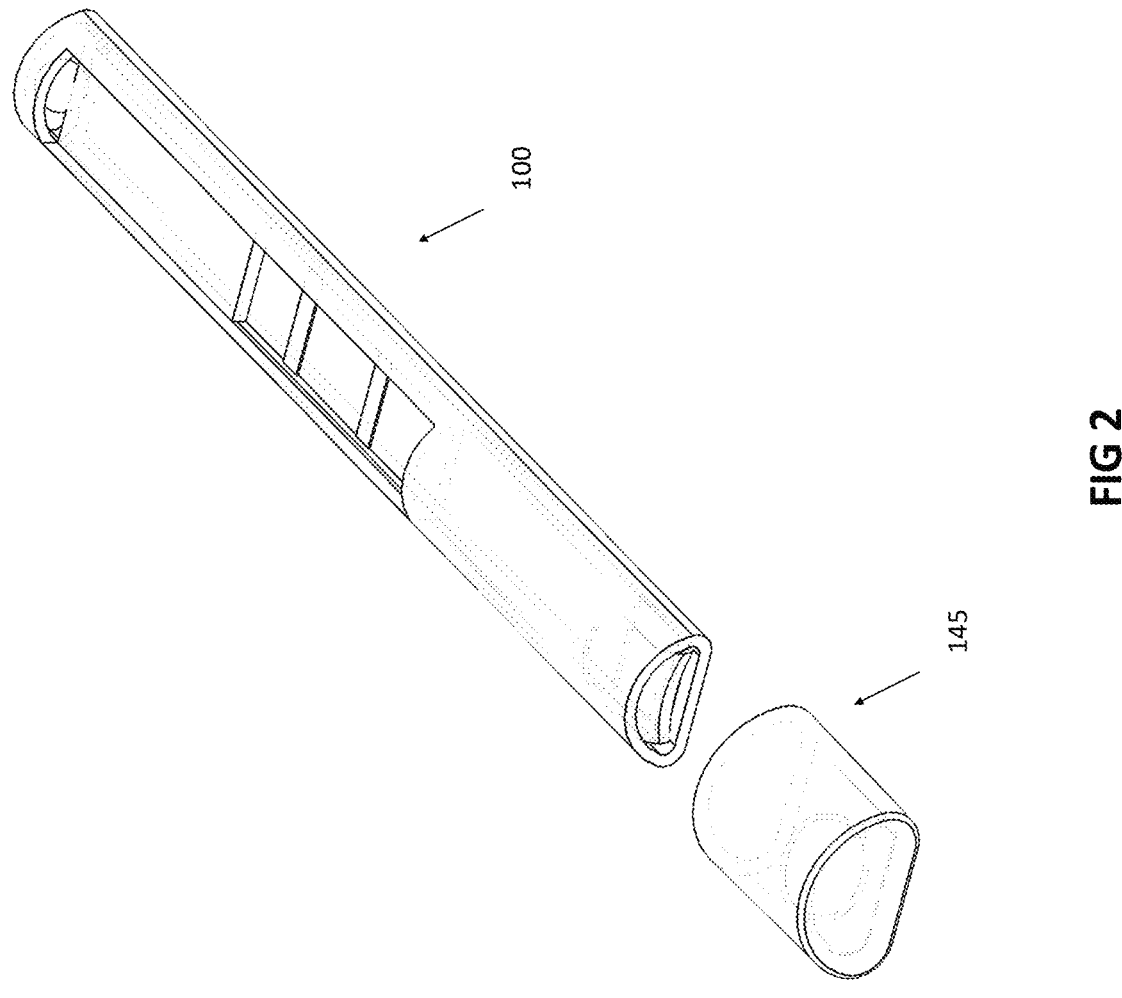
FIG. 2 depicts an orthogonal view of the assay tube and the reagent cap according to embodiments of the present invention.

FIG. 2 depicts an orthogonal view of the assay tube 100 and the reagent cap 145 according to embodiments of the present invention. One can more readily see the viewing opening 115 and cross-section of the assay tube 100 and reagent cap 145 in this figure.

FIG. 3 depicts an orthogonal view of an external portion of a curved assay tube according to embodiments of the present invention. An orthogonal view of the external portion of the curved assay tube 310 is shown along with an end view 320.

FIG. 4 depicts an orthogonal view of an external portion of a trapezoidal assay tube according to embodiments of the present invention. An orthogonal view of the external portion of the trapezoidal assay tube 410 is shown along with an end view 420.

Figure 5:
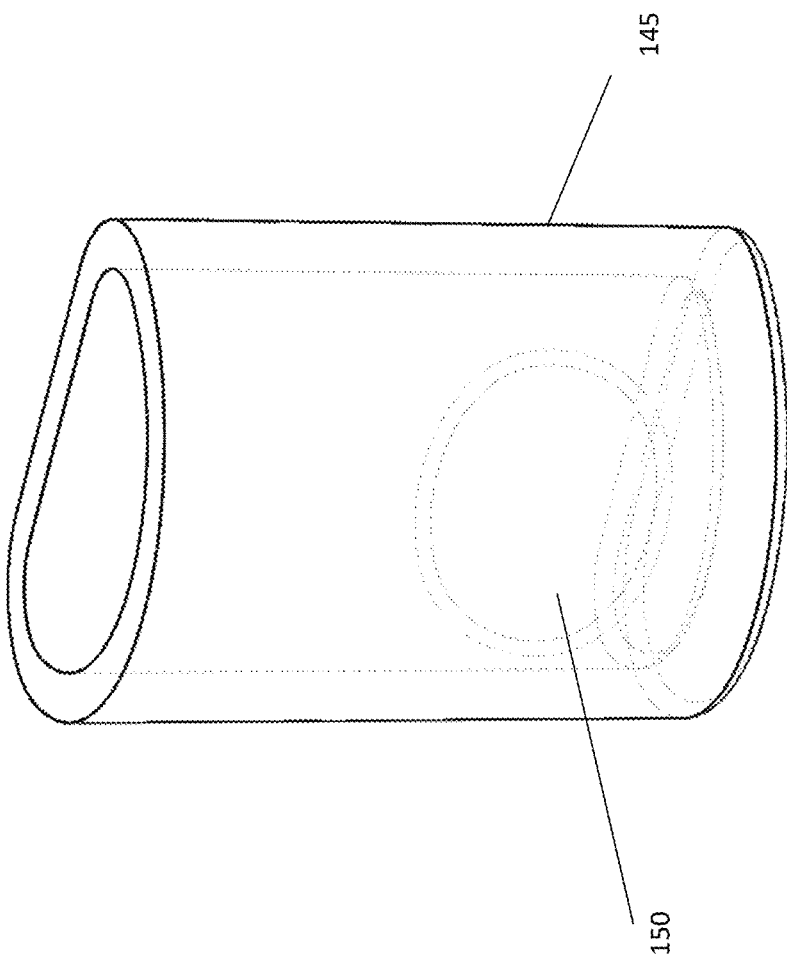
FIG. 5 depicts an orthogonal view of the reagent cap according to embodiments of the present invention.

FIG. 5 depicts an orthogonal view of the reagent cap 145 according to embodiments of the present invention. Again, the reagent cap 145 may include a capsule 150 containing buffer in one embodiment. An alternate embodiment is shown in FIG. 7 below.

Figure 6:
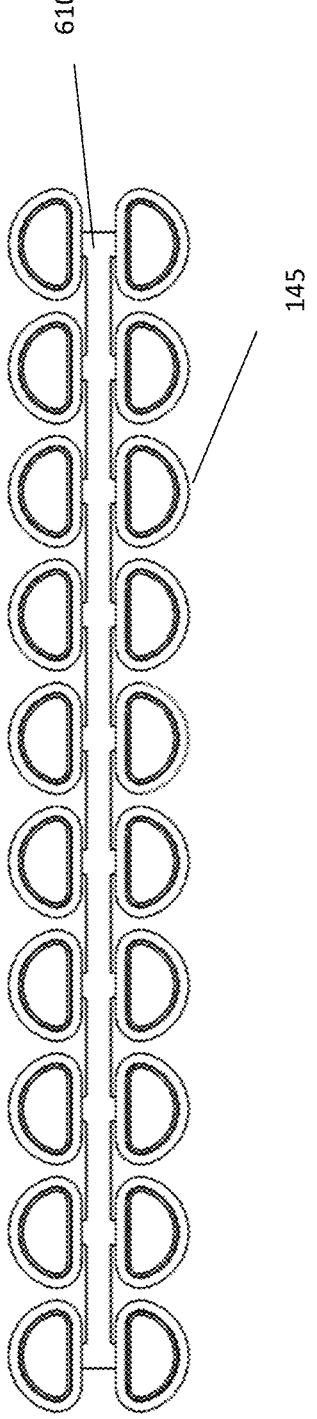
FIG. 6 depicts a top down view of 20 reagent caps according to embodiments of the present invention.

FIG. 6 depicts a top down view of 20 reagent caps 145 according to embodiments of the present invention. These reagent caps 145 may be made by a molding process where a central spine 610 is used to flow reagent cap material into a mold for creating reagent caps 145. Because of the molding method used, each reagent cap 145 will have an imperceptible nib on the interior portion of the reagent cap 145 where the material flows to create the reagent cap 145. This nib has the beneficial purpose of helping secure the reagent cap 145 to the assay tube 100 when placed on the assay tube 100.

Figure 7:
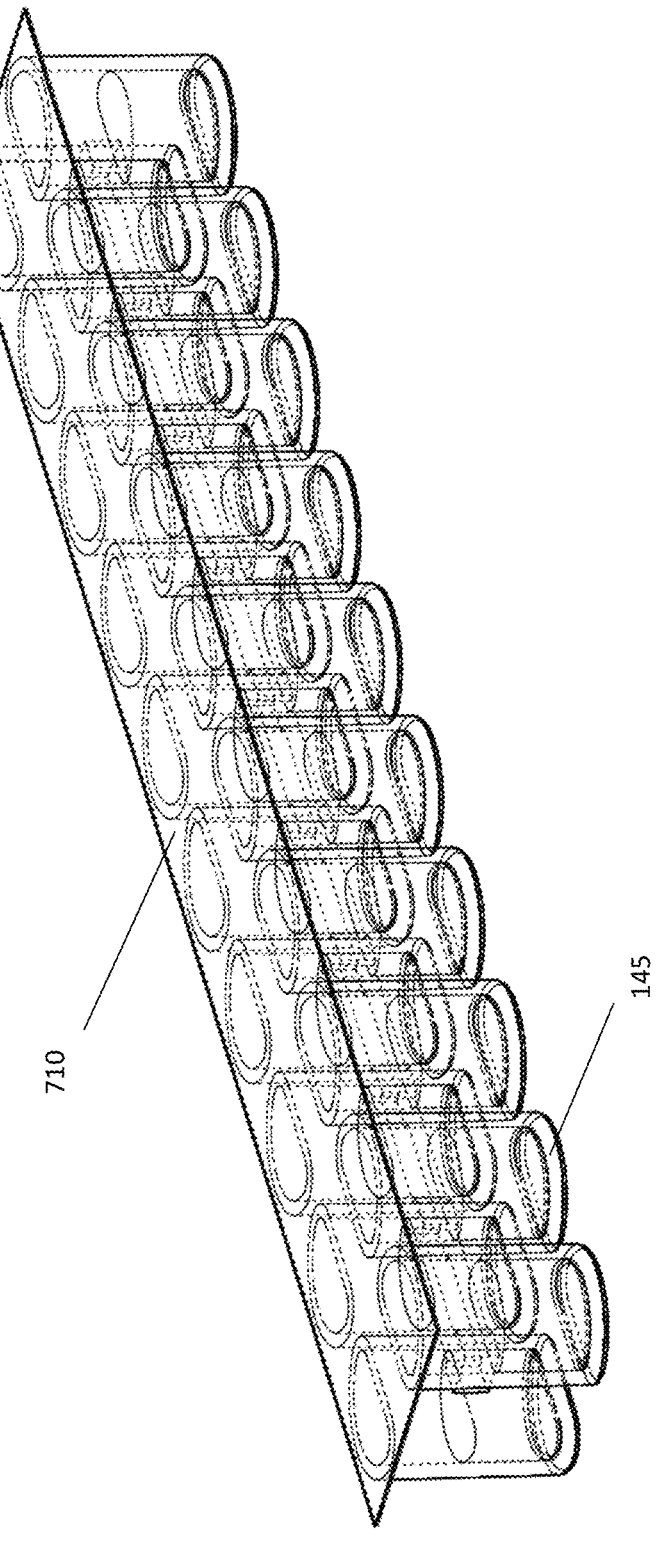
FIG. 7 depicts an orthogonal view of 20 reagent caps containing buffer covered by a film according to embodiments of the present invention.

FIG. 7 depicts a top down view of 20 reagent caps 145 containing buffer covered by a film 710 according to embodiments of the present invention. In an exemplary embodiment, the film 710 is PVC-coated aluminum. The PVC-coated aluminum film 710 may have printing placed upon it, such as instructions for use. The PVC-coated aluminum film 710 is adhered to the reagent caps 145 by heating the PVC-coated aluminum film 710 on top of the reagent caps 145. In this alternate embodiment of the reagent cap 145, the reagent cap 145 does not use a capsule 150 containing a buffer. Instead, the buffer is placed directly into the reagent cap 145, and a film 710 is placed on top of the reagent caps 145 and sealed to the reagent caps 145 to hold the buffer in place until the reagent cap 145 is placed onto the assay tube 100. Placing the reagent cap 145 onto the assay tube 100 pierces the film 710 releasing the buffer.

Figure 8:
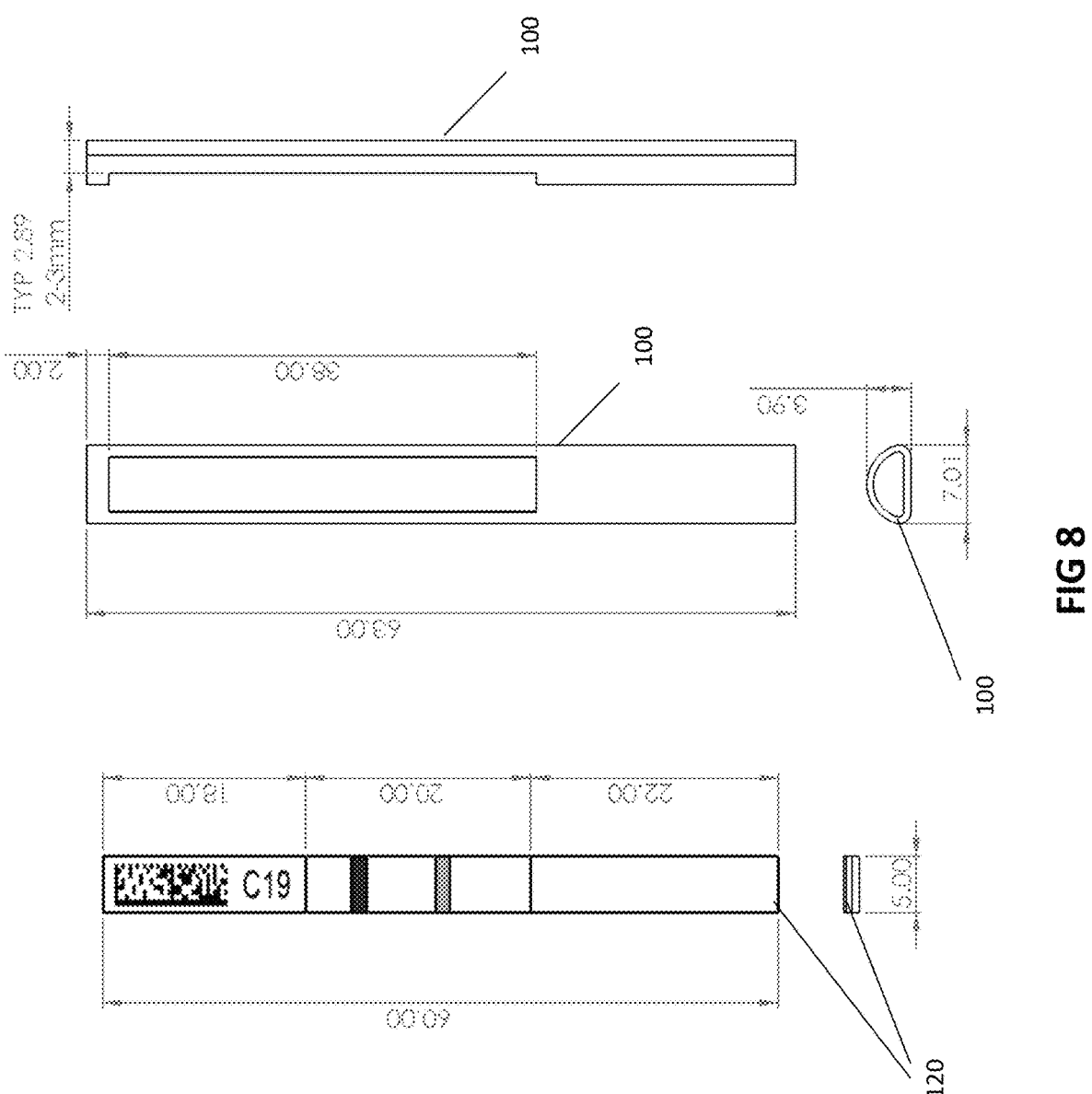
FIG. 8 depicts a standardized sizing for the assay tube according to embodiments of the present invention.

FIG. 8 depicts a standardized sizing for the assay tube 100 according to embodiments of the present invention. Moving to a standardized sizing of test kits and specifically assay tubes 100 permits for ease of storage, sales, and distribution. Measurements shown are all in millimeters and all are approximate with some variation being both acceptable and expected.

Figure 9:
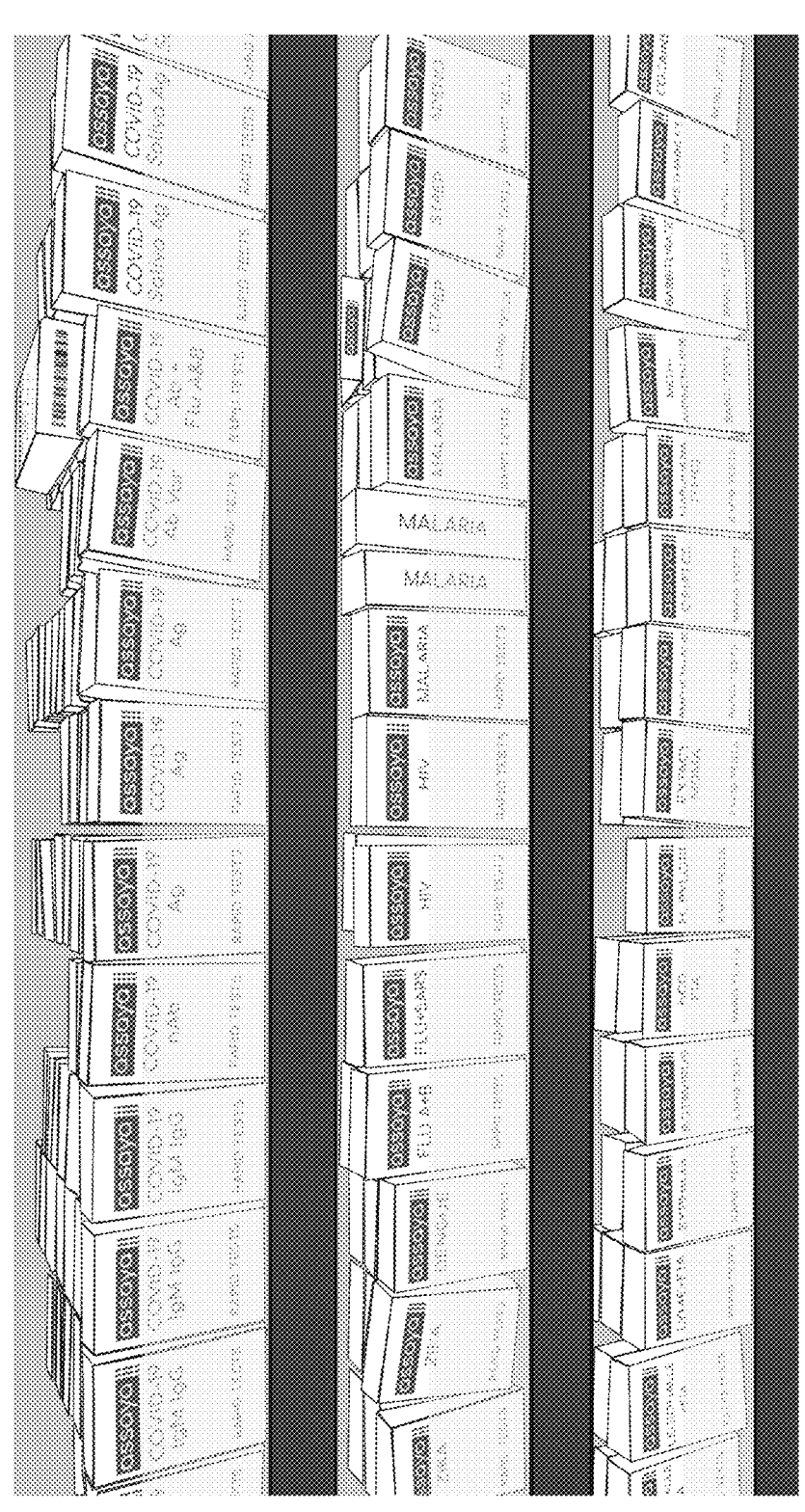
FIG. 9 illustrates a display of test kit packages that may be stored, sold, or marketed according to embodiment of the present invention.

FIG. 9 illustrates a display of test kits that may be stored, sold, or marketed according to embodiment of the present invention. The sizing of the assay tubes 100 is not coincidentally approximately the same size as a cigarette, so they may be packaged in packages of 20, for example, in a package roughly the size of a cigarette pack. Existing cigarette marketing shelving may thus be used to store and sell the test kits (each test kit comprising a set number of assay tubes 100 and associated reagent caps 145).

Figure 10:
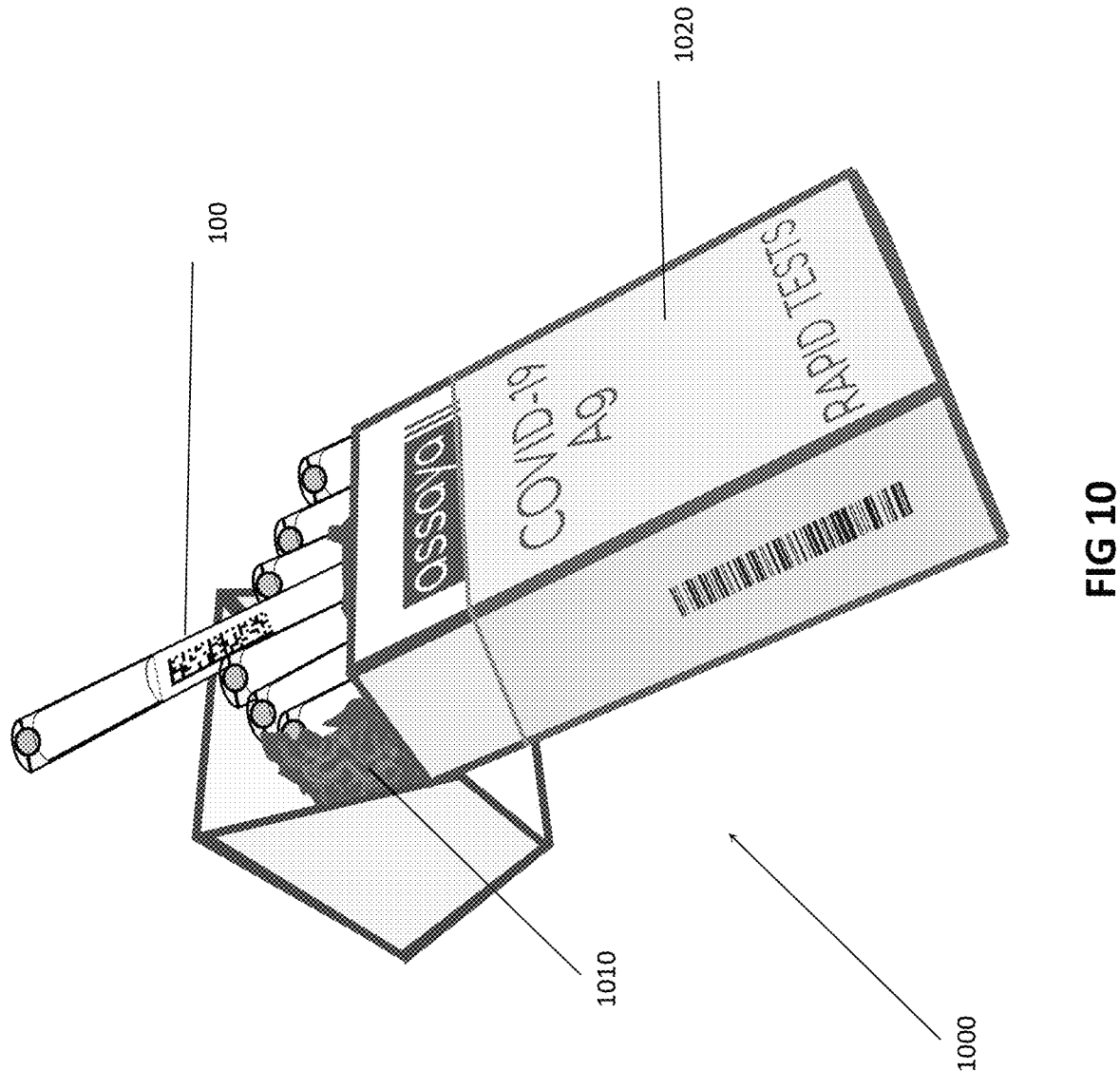
FIG. 10 illustrates a package for storing a plurality of test kits according to embodiment of the present invention.

FIG. 10 illustrates a package 1000 for a plurality of test kits 100 and 145 according to embodiment of the present invention. The package resembles a traditional cigarette pack with assay tubes 100 and reagent caps 145 being stored with the package 1000 similar to the storage of cigarettes. The package contains an inner foil 1010 and external wrap 1020 which, in conjunction with the desiccant in the assay tubes 100, reduces moisture within the package 1000. This packaging allows for safe and easy storage and sales of test kits.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A test kit, comprising:
an assay tube including:
    a sample opening in the assay tube for receiving a sample; and
    a lateral flow assay ("LFA") test strip in the assay tube and in communication with the sample opening; and
    a reagent cap for placing over the sample opening of the assay tube to close the sample opening of the assay tube, the reagent cap including a liquid buffer covered by a layer,
    wherein when the reagent cap is placed over the sample opening of the assay tube the layer is pierced, and the liquid buffer is released over the sample to carry an analyte over the LFA test strip.

2. The test kit of claim 1, wherein the sample opening is roughened to pierce the layer.

3. The test kit of claim 1, further comprising a viewing opening in the assay tube above at least a portion of the LFA test strip.

4. The test kit of claim 1, wherein the buffer within the reagent cap is contained within a capsule.

5. The test kit of claim 1, wherein the layer in the reagent cap comprises a film sealing the buffer within the reagent cap.

6. The test kit of claim 1, wherein the assay tube further comprises a desiccant within the assay tube.

7. The test kit of claim 6, wherein the desiccant within the assay tube changes color in presence of moisture.

8. The test kit of claim 1, further comprising an absorbent material in proximity to the sample opening in the assay tube.

9. The test kit of claim 8, wherein the absorbent material filters virus particles out of exhaled air received into the sample opening.

10. The test kit of claim 1, further comprising a container holding a plurality of assay tubes and reagent caps.

11. The test kit of claim 1 wherein the sample is blood.

12. The test kit of claim 1, wherein the sample is from epithelial cells of a patient.

13. The test kit of claim 12, wherein the epithelial cells are from one of a patient's nasal cavity and oral cavity.

14. The test kit of claim 12, wherein the epithelial cells are from one of: a patient's skin, a patient's vagina, a patient's anus, a patient's excreta.

15. The test kit of claim 1, wherein the test kit is configured to collect the sample from a fluid.

16. A method of using a test kit comprising:
receiving a sample at a sample opening in an assay tube, the assay tube including a lateral flow assay ("LFA") test strip;
closing the assay tube by placing a reagent cap over the sample opening, the reagent cap including a liquid buffer protected by a layer;
piercing the layer protecting the liquid buffer when the reagent cap is placed over the sample opening of the assay tube, such that the liquid buffer is released over the sample to carry an analyte over the LFA test strip.

17. The method of claim 16, wherein the layer protecting the liquid buffer within the reagent cap is a capsule.

18. The method of claim 16, further comprising:
filtering virus particles out of exhaled air received into the sample opening using an absorbent material in proximity to the sample opening in the assay tube.

19. The method of claim 16, wherein the sample is blood.

20. The method of claim 16, wherein the sample is from epithelial cells of a patient, and the epithelial cells are from one of: a nasal cavity, an oral cavity, skin, vagina, anus, or excreta.

* * * * *